United States Patent [19]

Cronjaeger

[11] Patent Number: 4,905,683

[45] Date of Patent: Mar. 6, 1990

[54] RESPIRATOR MASK FOR POSITIVE PRESSURE RESPIRATOR EQUIPMENT

[75] Inventor: Ralf Cronjaeger, Lübeck, Fed. Rep. of Germany

[73] Assignee: Drägerwerk Aktiengesellschaft, Lübeck, Fed. Rep. of Germany

[21] Appl. No.: 73,909

[22] Filed: Jul. 10, 1987

Related U.S. Application Data

[63] Continuation of Ser. No. 843,103, Mar. 24, 1986, abandoned.

[30] Foreign Application Priority Data

Mar. 22, 1985 [DE] Fed. Rep. of Germany ....... 3510302

[51] Int. Cl.[4] .............................................. A61L 10/00

[52] U.S. Cl. .......................... 128/202.22; 128/206.24; 128/207.12

[58] Field of Search ...................... 128/201.23, 206.24, 128/202.72, 201.75; 73/40, 40.7, 40.5 R, 49.2, 49.8, 52; 12/201.28, 204.26, 205.12, 205.13, 205.17, 205.25, 206.12, 207.12

[56] References Cited

U.S. PATENT DOCUMENTS

| | | | |
|---|---|---|---|
| 2,420,372 | 5/1947 | Heidbrink | 73/40 |
| 2,738,669 | 3/1956 | Silverman et al. | 73/40 |
| 3,486,366 | 12/1969 | Jackson | 73/40 |
| 3,580,051 | 5/1971 | Blevins | 73/40 |
| 4,146,025 | 3/1979 | Warncke et al. | 128/201.23 |
| 4,253,328 | 3/1981 | Pasternack | 73/40.7 |
| 4,574,799 | 3/1986 | Warncke | 128/206.24 |

FOREIGN PATENT DOCUMENTS

| | | | |
|---|---|---|---|
| 539204 | 11/1931 | Fed. Rep. of Germany | 73/40 |
| 668611 | 11/1934 | Fed. Rep. of Germany | 73/40 |
| 698045 | 10/1940 | Fed. Rep. of Germany | 73/40 |
| 705843 | 4/1941 | Fed. Rep. of Germany | 73/40 |
| 730322 | 12/1942 | Fed. Rep. of Germany | 73/40 |
| 737593 | 6/1943 | Fed. Rep. of Germany | 73/40 |
| 897951 | 10/1953 | Fed. Rep. of Germany | 73/40 |
| 1232474 | 1/1967 | Fed. Rep. of Germany | 73/40.7 |
| 1559680 | 1/1970 | Fed. Rep. of Germany | 73/40 |
| 1706047 | 10/1970 | Fed. Rep. of Germany | |
| 2550594 | 5/1977 | Fed. Rep. of Germany | 73/40 |
| 724174 | 4/1932 | France | 73/40 |
| 1191793 | 5/1970 | United Kingdom | 128/206.24 |
| 1215218 | 12/1970 | United Kingdom | |

*Primary Examiner*—Max Hindenburg
*Assistant Examiner*—K. M. Reichle
*Attorney, Agent, or Firm*—McGlew & Tuttle

[57] ABSTRACT

A respirator mask for positive pressure respirator equipment comprises several peripheral seal edges around the face of the mask wearer. It must be assured that in case of possible leaks of the seal edges no respiratory gas, in particular respiratory gas with increased oxygen concentration, escapes into the open. To check that there are no leaks of respiratory gas past the seal edges, one of the sealing cavities defined by the seal edges in the mask is connected to a connecting line. This cavity defines a control chamber. A flow indicating device is connected to the connecting line and is placed so that it is visible to the wearer. A valve is positioned in a part of the mask bounding the interior of the control chamber. The valve can be actuated to permit the flow of gas, for example exhaled gas, into the control chamber and out through the connecting line and flow indicating device. The wearer can determine what a normal flow value should be and, if the flow observed on the flow indicating device falls below this value, it is assumed that a leak has developed.

7 Claims, 3 Drawing Sheets

RESPIRATOR MASK FOR POSITIVE PRESSURE RESPIRATOR EQUIPMENT

This application is a continuation of application Ser. No. 843,103, filed Mar. 24, 1986, now abandoned.

FIELD AND BACKGROUND OF THE INVENTION

This invention relates in general to respirators and in particular to a new and useful respirator mask having one or more sealed areas within the mask located within a surrounding peripheral seal with the wearer's face and a connecting line therein which extends outwardly to the surrounding air and which contains a flow indicating device.

A similar respirator mask is known from German AS 17 08 047. The known respirator mask has a double seal edge by which protection of the apparatus wearer from penetrating pollutants is achieved in that there is at least one connection between the mask interior and the space between the two seal edges through which exhalation air is conducted into this space. The space between the two seal edges is always filled with exhalation air. In case of possible leaks between the seal edges and the skin surface of the mask wearer, penetration of outside air into the interior of the mask is avoided. If ambient air can penetrate into the space between the seal edges, this air is flushed out with the next exhalation.

Such a respirator mask is suitable for use with compressed air equipment, as the gases flushed out as part of the exhalation air are harmless with respect to their composition and also do not constitute a limitation to the duration of use of the compressed air equipment. By the use of the known respirator mask in conjunction with the circulation respirator apparatus in positive pressure operation, the discharge of the exhalation air through the space between the seal edges into the open would, in the course of time, cause a loss of inert gas, so that the oxygen concentration in the respiratory system increases. Hence the oxygen concentration in the exhalation air which is breathed out of the sealed interstices into the open also increases. This results in an unrecognizable danger to the user of the apparatus if he is near an open flame. if, moreover, in the course of using the known respirator mask with a circulation respirator apparatus the seal edges would somehow loosen or become detached, again exhalation air with a high oxygen concentration would escape through a greater leak at the seam frame of the mask.

SUMMARY OF THE INVENTION

The invention provides an improved respirator mask in which it is indicated to the wearer of a respirator apparatus when leaks occur in the cavities defined by the seal edges, so that he is given a possibility to check the tight fit of the respirator mask.

According to the invention, the problem is solved in that at least one of the cavities is connectable as a control chamber to a connecting line leading into the surrounding area and containing a flow indicating device. When compressed air equipment is connected to the respirator mask, the cavity present between the seal edges at the mask edge forms a control chamber. If a circulation respirator apparatus is connected to the respirator mask, the space between the inner and outer masks forms the control chamber.

The advantage of the invention resides in that after applying the respirator mask, the wearer of the mask, with positive pressure respirator equipment, can first check the tight abutment of the seal edges. Any occurring leaks can immediately be recognized during use of the mask. The wearer can take suitable counter measures to close the leak or to withdraw from the danger area.

If the seal edges of the respirator mask apply tightly on the wearer's face, no flow is indicated in the flow indicator.

Preferably the mask wearer can check the sealing function of the seal edges at any time by actuating a valve. This is done either by opening a valve by hand, or appropriately by a flap located at the connecting piece of the respirator mask in the respiration flow. Thus the mask wearer himself can check the tightness of the mask, if necessary, by actuating the valve by hand, or the seal test takes place automatically with every exhalation or inhalation.

If in a circulation respirator apparatus the positive pressure control fails, negative pressures may occur in the mask, as in an ordinary vacuum respirator apparatus. In order that, in such a case, no ambient air can penetrate into the mask via the connecting line even if there is a leak between the seal edges and the skin of the apparatus wearer or during actuation of the valve, the flow indicating device is advantageously designed as a check valve.

To be able to monitor the leakage, the flow indicating device is preferably disposed in the region of the sight window.

To avoid that in case of a leak the oxygen-rich breathing gas escaping from the flow indicator will lead to high oxygen concentrations near the mask wearer's head, a development of the invention provides that the end piece of the connecting line discharges in the vicinity of the breathing bag of a circulation apparatus. The periodic motions of the breathing bag provide for thorough mixing of the oxygen-rich respiratory gas with the ambient air, so that there can be no danger caused by excessive oxygen concentration.

Accordingly, it is an object of the invention to provide a respirator mask which operates with pressure equipment and which includes at least one or more defined sealing areas within an outer facial sealing of the mask to the wearer which has a connecting line through which gases flowing into the area will be passed to the outside and which has a flow indicator so as to give the wearer an idea of the sealing conditions existing with the mask.

A further object of the invention is to provide a mask having means for indicating the leakage thereof and which may be easily detected by the wearer such as by a visible indication thereof.

A further object of the invention is to provide a respirator mask which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
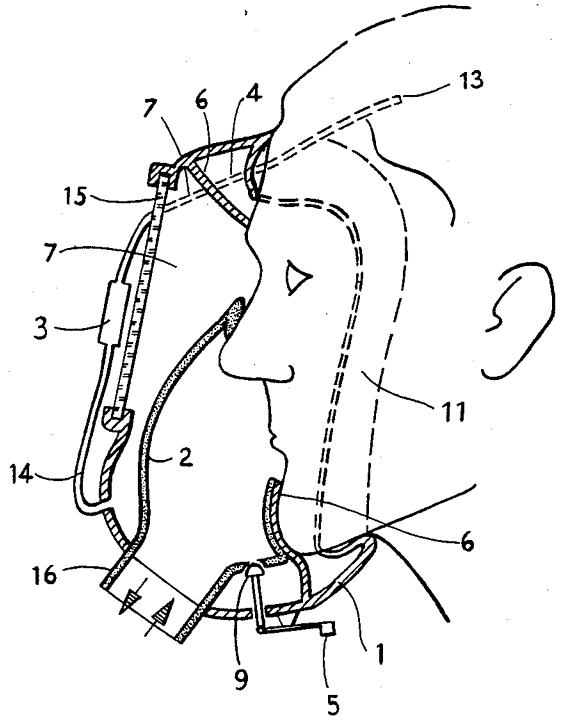
FIG. 1 is a sectional view of a respirator mask for a circulation apparatus with positive pressure constructed in accordance with the invention.

Referring to the drawings in particular the invention embodied therein comprises a respirator mask which has an outer sealing edge 11 which is sealed around the wearer's face. In accordance with the invention, the mask includes one or more cavities defined within the sealed area surrounded by the edge 11 which are connected by a connecting line 14 which has a discharge 13 to the surrounding atmosphere and which is provided with a flow indicator 3 which indicates flow from these sealed cavities and provides an indication of the gas-tight fit of the mask.

Figure 3:
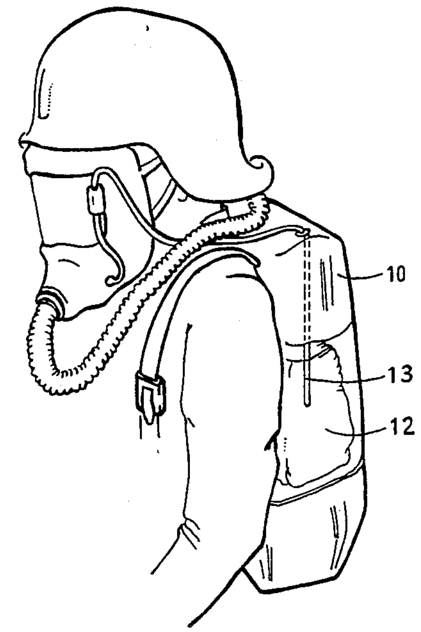
FIG. 3 is a view similar to FIG. 1 of the respirator mask with positive pressure circulation apparatus on the wearer.

In FIGS. 1 and 3, the respirator mask is illustrated for the wearer of a circulation respirator apparatus in positive pressure operation. It comprises a full mask body 1 and an internal half mask 2, the mask body 1 being arranged tightly fitting around the face of the mask wearer by means of the seal edges 6 and 11. A first chamber 4 is formed between the edges 6 and edge 11. At the same time, the half mask 2 covers the nose-mouth region of the wearer. A sight window 15 is cut into the mask body 1 in the sight region of the mask wearer. At a connecting piece 16 a circulation respirator apparatus 10 is connected as shown in FIG. 5. The mask interior space or second chamber 7 is enclosed between the inner seal edge 6 of the mask body 1 and of the half mask 2. The space 7 serves as the control chamber or cavity for checking whether the seal outer peripheral seal 11 and inner seal edge 6 tightly enclose the face contour of the mask wearer. Connected at the mask interior 7 via a connecting line 14 is the flow meter 3 which is arranged in the sight region of the sight window 15. The discharge 13 of the connecting line 14 is passed outside the mask body 1 to an outflow point as far away from the mask wearer as possible, advantageously in the vicinity of the breathing bag 12 of the respirator apparatus 10. In the lower region of the half mask 2 valve means are disposed which include in FIG. 1 a lever 5 pivoting on a fulcrum 19 and a valve member 9 which can be opened by moving the lever 5 so that the respiratory air present in the half mask 2 can flow under positive pressure into the mask interior 7. If the seal edges 6 and 11 apply tightly on the skin surface of the apparatus wearer everywhere, this air can flow out into the open only via the connecting line 14, the flow member 3 and the discharge 13. The mask wearer can in this case check the flow of the test air quantity intentionally flowing into the mask interior 7 and thus ascertain the tightness of the seal edges 6,11.

When the valve member 9 is closed and when the seal edges 6,11 as well as the half mask 2 fit tightly everywhere, the apparatus wearer will detect no flow in the flow meter 3. If, however, the seal edge of the half mask 2 should begin to leak at any point and should the respiratory gas contained in it under positive pressure flow into the mask interior 7 due to the leak, the mask wearer will observe a corresponding flow indication.

Figure 2:
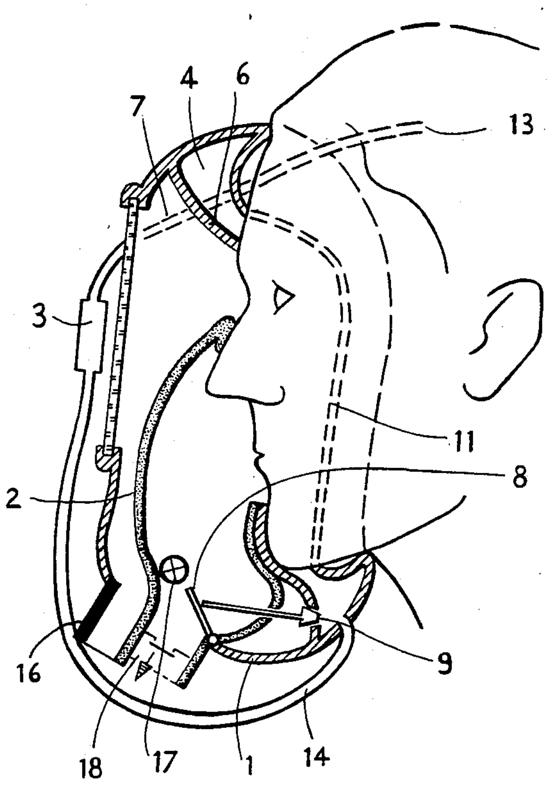
FIG. 2 is a view similar to FIG. 1 of the respirator mask for compressed air equipment.

In FIG. 2, the same reference numerals as in FIG. 1 designate the same or corresponding parts. It is noted that as with the embodiment of FIG. 1, an outer annular sealed cavity 4 is defined between the outer seal edge 11 and the inner seal edge 6. In the embodiment of FIG. 2, the valve member 9 opens and closes a hole in the inner seal edge 6 to open and close communication between the mask interior 7 and the sealing cavity 4. The arrangement of FIG. 2 also includes a full mask body 1 which carries the inner and outer seal edges 6, 11, a half mask 2, a connecting line 14 with indicator 3 and discharge 13. In the embodiment of FIG. 2, the connecting line 14 is connected to the sealing cavity 4 rather than to the mask interior 7. Thus the sealing cavity 4 rather than the mask interior 7 forms the control chamber in FIG. 2.

As discussed above, the valve means of the embodiment of FIG. 1 includes a valve member 9 which is opened by moving the lever 5 so as to seat and unseat the valve member. This valve means provides communication between mask interior 7 and the interior above the half mask 2. The valve means of FIG. 2 includes a flap 8 operating a valve member 9 which is seated and unseated upon the movement of flap 8 due to the provision of a connection member 22 connecting flap 8 to valve member 9.

The embodiment of FIG. 2 seal edge 11 acts as the control chamber seal or cavity seal and seal edge 6 cooperates with cavity seal 11 to define a control chamber or cavity 4. Thus the outer chamber 4 acts as the control chamber instead of the mask interior 7 acting as the control chamber as in the embodiment of FIG. 1.

Instead of having actuate the opening of the valve means by hand, It may be provided, as shown in FIG. 2, to arrange a flap 8 in the breathing stream. Flap 8 operates valve member 9, which connects the mask interior 7 with the control member or cavity 4 formed between the outer peripheral seal edge 11 and seal edge 6 of the mask body 1. The respiratory air supplied by the compressed air equipment enters the mask interior 7 at the connecting piece 16. Thence, during inhalation, it passes via a directional valve 17 to the respiratory organs of the wearer. In so doing, it actuates flap 8 and opens valve 9, so that the apparatus wearer can observe with every inhalation a defined, constant flow quantity in the flow meter 3 if the seal edges 6,11 fit tightly everywhere. Exhalation occurs via an exhalation valve 18 into the open.

While specific embodiments of the invention have been shown and described in detail to illustrate the application of the principles of the invention, it will be understood that the invention may be embodied otherwise without departing from such principles.

What is claimed is:

1. A respirator mask comprising: a half mask having an interior engageable over the nose and mouth of a wearer and having a peripheral resilient seal edge engageable on the wearer's face and a respiratory air connecting piece leading out of the said half mask, said connecting piece communicating with said half mask interior; an outer full mask body over said half mask, said outer full mask body being sealed with the connecting piece, said outer full mask body having an outer peripheral seal edge resiliently engageable around and sealable about the wearer's face and an inner seal edge engageable around and sealable with the wearer's face, said full mask body having a front wall with a viewing window through which the wearer can see when wearing the respirator mask, said full mask body defining a first chamber between said full mask body outer peripheral seal edge and said full mask body inner seal edge and said full mask body cooperating with said half mask to define a second chamber between said full mask body inner seal edge and said half mask seal edge; a connecting line having one end connected into one of said first chamber and said second chamber and discharging into the ambient, said connecting line extending out of said full mask body and past said viewing window, said connecting line also having a discharge end spaced away from said viewing window for the discharge into the ambient; a flow indicator in said connecting line adjacent said viewing window for indicating a flow which can be seen by the wearer when wearing the respirator mask; and, valve means for opening and closing communication between said respiratory air connecting piece and said one of said first chamber and said second chamber so that respiratory air may pass into said one of said first chamber and said second chamber and through said connecting line to influence said flow indicator.

2. A respirator mask according to claim 1, wherein said connecting piece also leads into and communicates with the outer full mask body, said one of said chambers is said second chamber, said valve means includes an opening providing communication between said first chamber and said second chamber, a flap is disposed in said half mask, a valve member covers said opening and is connected to said flap and said flap is moveable by inhalation and exhalation to selectively open and close the communication between said second chamber and said first chamber.

3. A respirator mask according to claim 1 further including a breathing bag connected to said connection piece located adjacent the discharge end of said connecting line.

4. A respiratory mask according to claim 1 further including lever means pivotally mounted on said full mask body for actuating said valve means.

5. A respirator mask comprising: a half mask having an interior engageable over the nose and mouth of a wearer and having a peripheral resilient seal edge engageable on the wearer's face and a respiratory air connecting piece leading out of the said half mask, said connecting piece communicating with said half mask interior; an outer full mask body over said half mask, said outer full mask body being sealed with the connecting piece, said outer full mask body having an outer peripheral seal edge resiliently engageable around and sealable about the wearer's face and an inner seal edge engageable around and sealable with the wearer's face, said full mask body having a front wall with a viewing window through which the wearer can see when wearing the respirator mask, said full mask body defining a first chamber between said full mask body outer peripheral seal edge and said full mask body inner seal edge and said full mask body cooperating with said half mask to define a second chamber between said full mask body inner seal edge and said half mask seal edge; a connecting line having one end connected into said second chamber and discharging into the ambient, said connecting line extending out of said full mask body and past said viewing window, said connecting line also having a discharge end spaced away from said viewing window for the discharge into the ambient; a flow indicator in said connecting line adjacent said viewing window for indicating a flow which can be seen by the wearer when wearing the respirator mask; and, valve means for opening and closing communication between said half mask interior and the second chamber so that respiratory air may pass into said second chamber and through said connecting line to influence said flow indicator.

6. A respirator mask comprising: a half mask having an interior engageable over the nose and mouth of a wearer and having a peripheral resilient seal edge engageable on the wearer's face and a respiratory air connecting piece leading out of the said half mask, said connecting piece communicating with said half mask interior; an outer full mask body over said half mask, said outer full mask body being sealed with the connecting piece, said outer full mask body having an outer peripheral seal edge resiliently engageable around and sealable about the wearer's face and an inner seal edge engageable around and sealable with the wearer's face, said full mask body having a front wall with a viewing window through which the wearer can see when wearing the respirator mask, said full mask body defining a first chamber between said full mask body outer peripheral seal edge and said full mask body inner seal edge and said full mask body cooperating with said half mask to define a second chamber between said full mask body inner seal edge and said half mask seal edge, said connecting piece also communicating with said second chamber; a connecting line having one end connected to said first chamber and discharging into the ambient, said connecting line extending out of said full mask body and past said viewing window, said connecting line also having a discharge end spaced away from said viewing window for the discharge into the ambient; a flow indicator in said connecting line adjacent said viewing window for indicating a flow which can be seen by the wearer when wearing the respirator mask; and, valve means for opening and clsoing communication between said second chamber and first chamber so that respiratory air may pass into said first chamber and through said connecting line to influence said flow indicator.

7. A respirator mask comprising: a half mask having an interior engageable over the nose and mouth of a wearer and having a peripheral resilient seal edge engageable on the wearer's face; and outer full mask body positioned about said half mask having an outer peripheral seal edge resiliently engageable around and sealable about the wearer's face, said full mask body having a front wall with a viewing window through which the wearer can see when wearing the respirator mask; a respirator air connecting piece sealed with respect to said outer full mask body and communicating with said masks' interiors; at least one chamber positioned between said seal edge of said half mask and said outer peripheral seal edge of said full mask body; a connecting line having one end connecting into said at least one chamber and also having a discharge end discharging into the ambient, said connecting line also extending outside of said full mask body and past said viewing window; a flow indicator in said connecting line adjacent said viewing window for indicating a flow which can be seen by the wearer through the viewing window of the respirator mask; and, valve means connected to said at least one chamber for opening and closing communication between said at least one chamber and said respiratory air connecting piece.

* * * * *